United States Patent
Bae et al.

(10) Patent No.: US 11,564,875 B2
(45) Date of Patent: Jan. 31, 2023

(54) COSMETIC COMPOSITION FOR SKIN REGENERATION

(71) Applicant: Amorepacific Corporation, Seoul (KR)

(72) Inventors: Il Hong Bae, Yongin-si (KR); Gibaeg Nam, Yongin-si (KR); Jaeyoung Ko, Yongin-si (KR); Jaewon You, Yongin-si (KR); Tae Ryong Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 25 days.

(21) Appl. No.: 17/280,947

(22) PCT Filed: Nov. 29, 2019

(86) PCT No.: PCT/CN2019/121885
§ 371 (c)(1),
(2) Date: Mar. 29, 2021

(87) PCT Pub. No.: WO2020/069683
PCT Pub. Date: Apr. 9, 2020

(65) Prior Publication Data
US 2021/0338553 A1  Nov. 4, 2021

(30) Foreign Application Priority Data

Oct. 1, 2018  (KR) ......................... 10-2018-0117152

(51) Int. Cl.
*A61K 8/35* (2006.01)
*A61Q 17/04* (2006.01)
*A61Q 19/08* (2006.01)

(52) U.S. Cl.
CPC ................ *A61K 8/35* (2013.01); *A61Q 17/04* (2013.01); *A61Q 19/08* (2013.01)

(58) Field of Classification Search
None
See application file for complete search history.

(56) References Cited

U.S. PATENT DOCUMENTS

2015/0328121 A1  11/2015  Chae et al.

FOREIGN PATENT DOCUMENTS

| CN | 103356439 A | 10/2013 | |
|---|---|---|---|
| CN | 103520039 A | 1/2014 | |
| CN | 103739660 A | 4/2014 | |
| CN | 106333907 A | 1/2017 | |
| CN | 106389141 A | 2/2017 | |
| CN | 107629104 A | 1/2018 | |
| CN | 111100179 A | 5/2020 | |
| JP | 2017-522354 A | 8/2017 | |
| KR | 10-2008-0090806 A | 10/2008 | |
| KR | 10-2014-0110376 A | 9/2014 | |
| KR | 10-2015-0057378 A | 5/2015 | |
| KR | 20160024092 A * | 3/2016 | ............. C07H 15/24 |
| KR | 10-1638818 B1 | 7/2016 | |
| KR | 10-1838354 B1 | 3/2018 | |
| WO | WO-2011083110 A2 * | 7/2011 | ............. A61K 31/728 |

OTHER PUBLICATIONS

Nguyen Thi Phuong Thao et al., "Triterpenoids from Camellia japonica and Their Cytotoxic Activity", Chem. Pharm. Bull., Jan. 2010, p. 121-124, No. 1, vol. 58.
International Searching Authority, International Search Report for PCT/CN2019/121885 dated Mar. 4, 2020 [PCT/ISA/210].
International Searching Authority, Written Opinion for PCT/CN2019/121885 dated Mar. 4, 2020 [PCT/ISA/237].
Extended European Search Report dated Apr. 21, 2022 in European Application No. 19868897.0.
Chanchal Garg et al., "Molecular mechanisms of skin photoaging and plant inhibitors", International Journal of Green Pharmacy, 2017, vol. 11, No. 2, pp. S217-S232 (16 pages total).
Eunsun Jung et al., "Effect of Camellia japonica oil on human type I procollagen production and skin barrier function", Journal of Ethnopharmacology, 2007, vol. 112, No. 1, pp. 127-131 (5 pages total).
Jin Young Kim et al., "Antioxidative and Antiaging Effects of Jeju Native Plant Extracts (II)", J. Soc. Cosmet. Scientists Korea, 2007, vol. 33, No. 3, pp. 165-173 (9 pages total).
Hideji Itokawa et al., "Two Triterpenes From the Flowers of Camellia Japonica", Phytochemistry, 1981, vol. 20, No. 11, pp. 2539-2542 (4 pages total).
Nguyen Thi Phuong Thao et al., "28-Nor-oleanane-type triterpene saponins from Camellia japonica and their inhibitory activity on LPS-induced NO production in macrophage RAW264.7 cells", Bioorganic & Medicinal Chemistry Letters, 2010, vol. 20, pp. 7435-7439 (5 pages total).
Kai Zhang et al., "Progress on ultraviolet resistance of natural products", Journal of Logistics University of PAP, Dec. 2018, vol. 27, No. 12, pp. 1043-1048 (6 pages total).

* cited by examiner

*Primary Examiner* — Nannette Holloman
(74) *Attorney, Agent, or Firm* — Sughrue Mion, PLLC

(57) ABSTRACT

A cosmetic composition includes a compound of the following chemical formula as an active ingredient. A method for regenerating skin includes applying an effective amount of the cosmetic composition to skin:

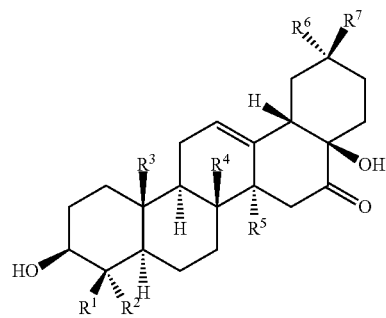

wherein $R^1$ to $R^7$ are independently a substituted or unsubstituted C1 to C20 alkyl group.

12 Claims, 6 Drawing Sheets

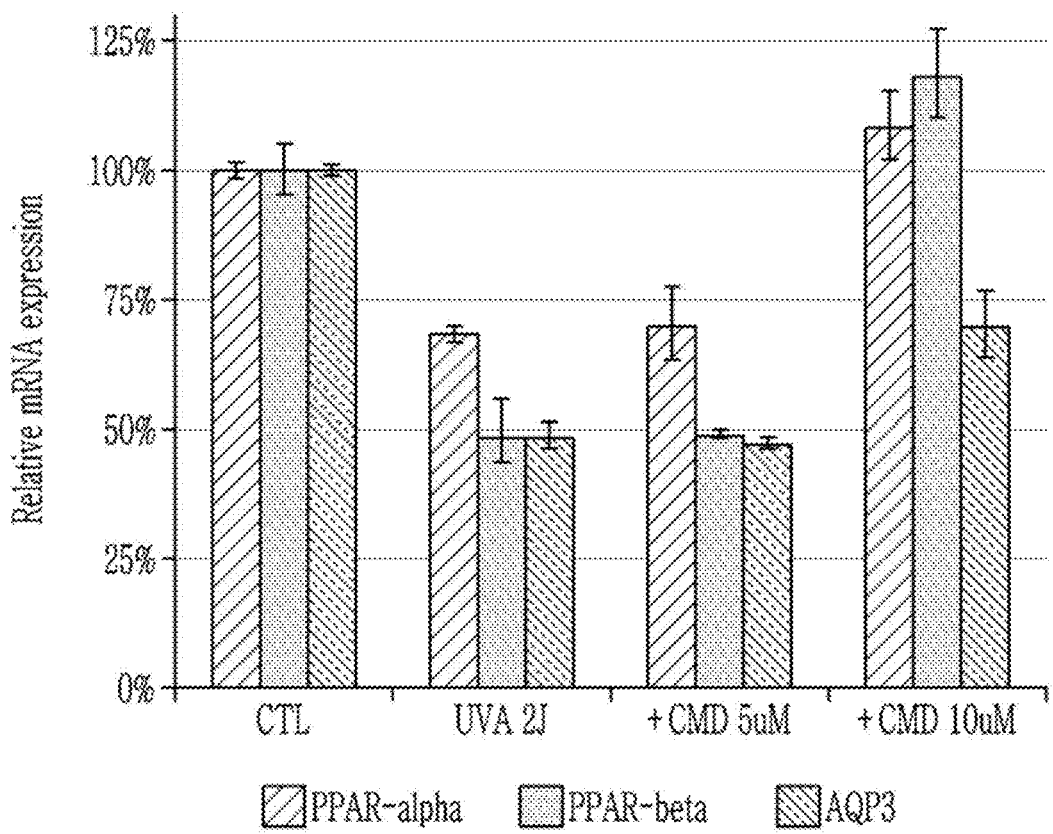
[Figure 1]

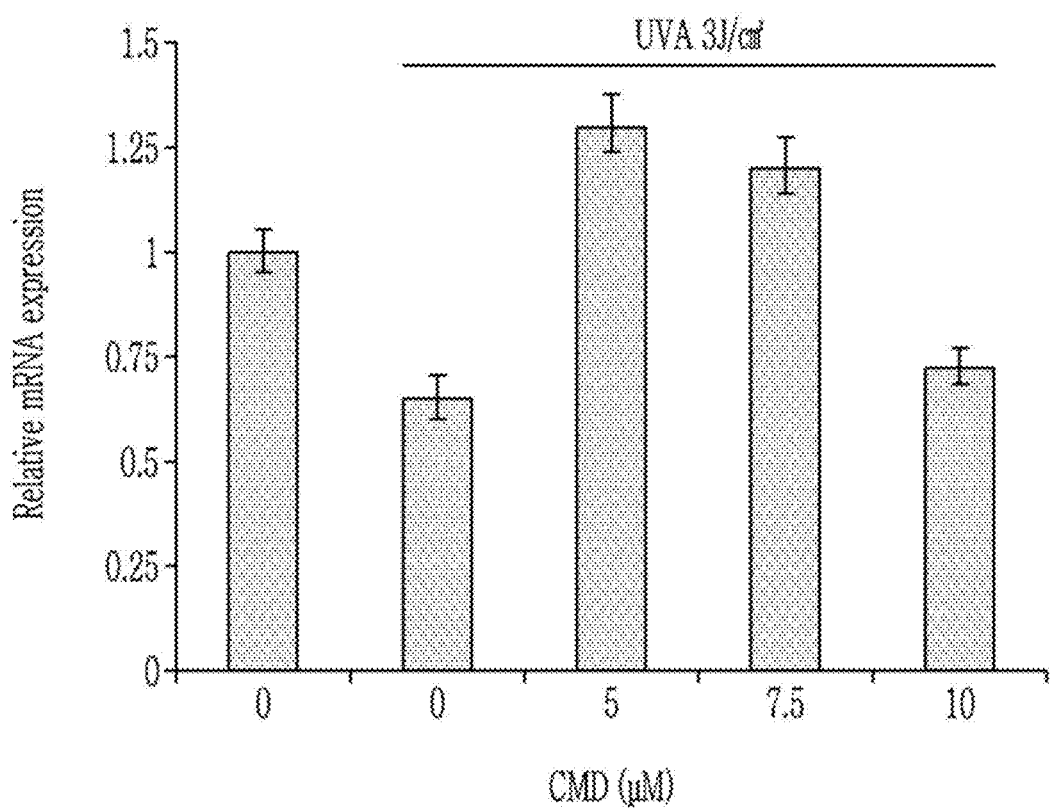
[Figure 2]

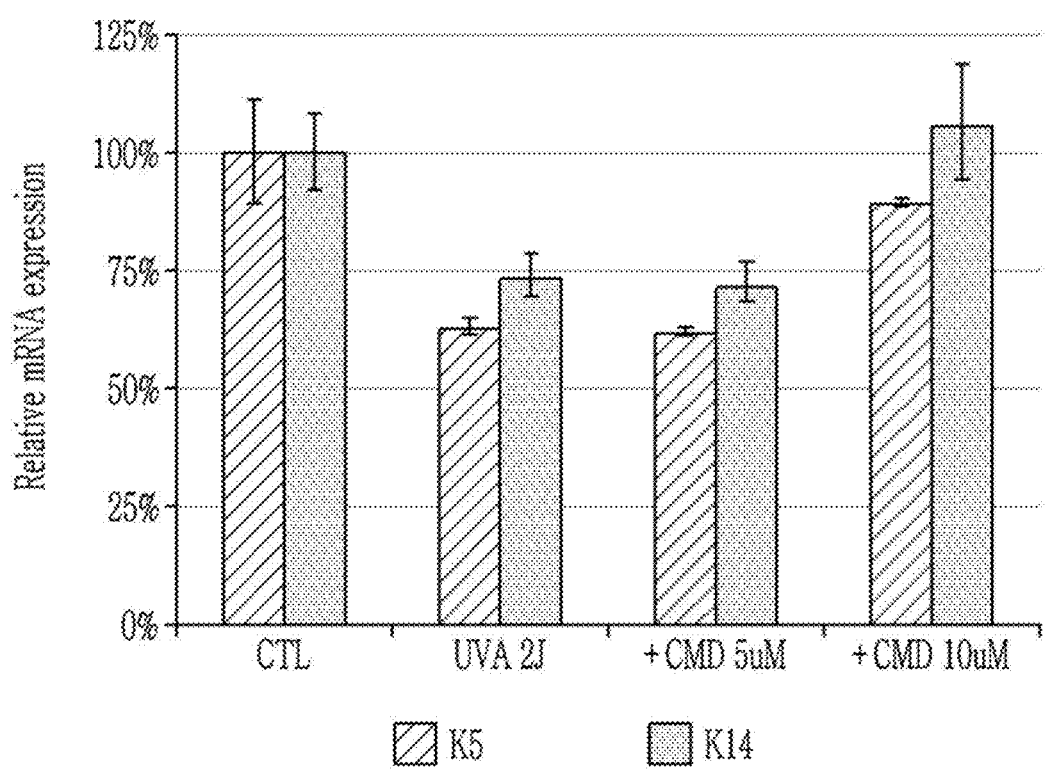
[Figure 3]

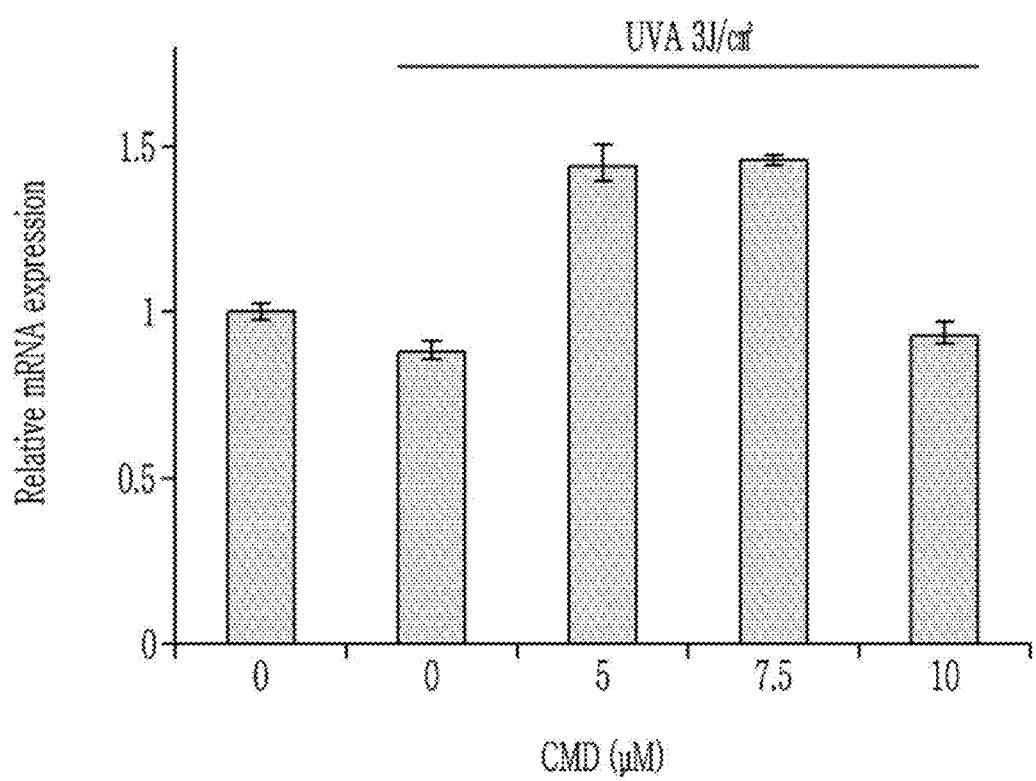
[Figure 4]

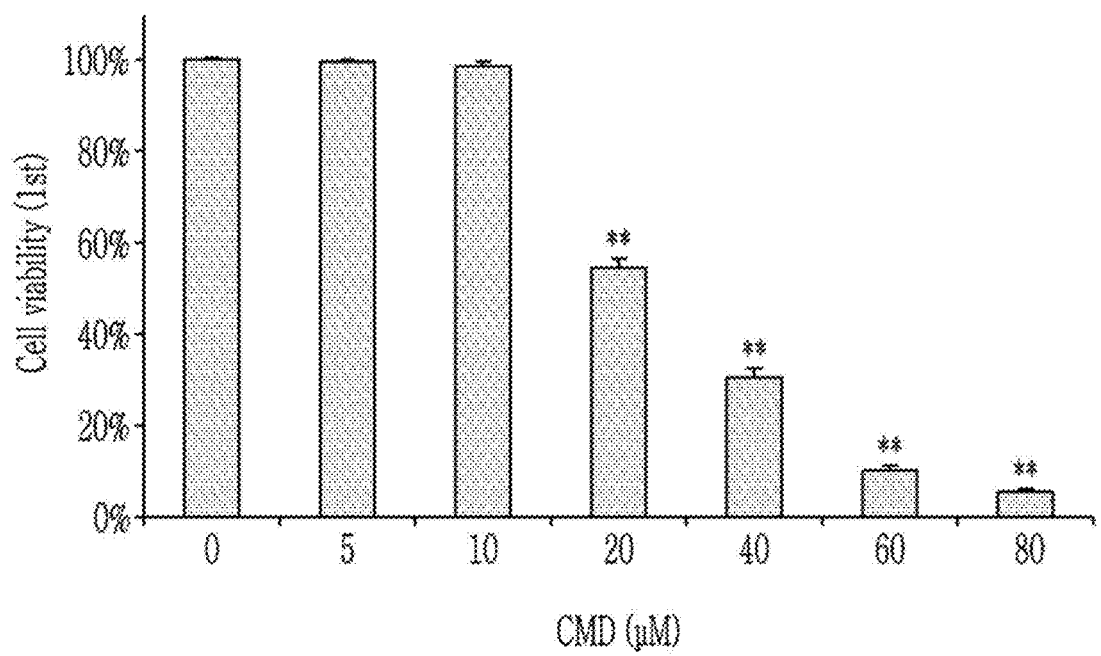
[Figure 5]

[Figure 6]
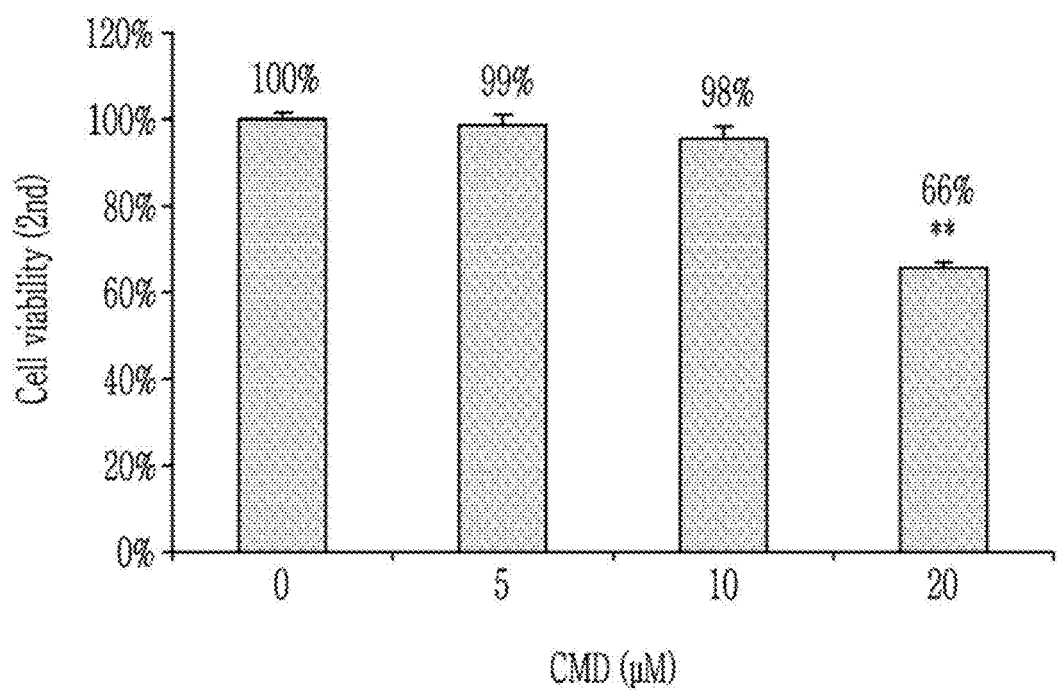

COSMETIC COMPOSITION FOR SKIN REGENERATION

CROSS REFERENCE TO RELATED APPLICATION

This is the U.S. national phase application based on PCT Application No. PCT/CN2019/121885, filed Nov. 29, 2019, claiming priority based on Korean Patent Application No. 10-2018-0117152 filed on Oct. 1, 2018, the entire contents of all of which are hereby incorporated by reference.

BACKGROUND

1. Field

This disclosure relates to a cosmetic composition and a method for regenerating skin by applying the cosmetic composition to skin.

2. Description of the Related Art

A skin is a tissue covering the outermost surface of a human body and thus functioning as a barrier and primarily protecting and defending the human body from external chemical and physical impacts. The skin consists of three layers such as epidermis, dermis, and subcutis, and the epidermis layer present at the outermost surface consists of 95% of keratinocyte. The keratinocyte of the epidermis efficiently defends the skin from viruses, chemical materials, and the like permeated thereinto, and secretes various cytokines and thus involves an inflammatory reaction and an immunoreaction of the skin. In addition, migration and proliferation of the keratinocyte may not only provide wound healing and skin regeneration but also lead a synthesis of collagen and thus play an important role of improving skin elasticity and forming a basement membrane. The collagen may have greater than or equal to 20 types depending on a α-chain, and Type I, III, IV, V, VI, and VII collagens are distributed in the human skin. Type I collagen mainly consists of greater than or equal to 85% of the dermis layer of the skin, Type IV collagen is a structural protein of the basement membrane, and accordingly, a synthesis of Type I and IV collagens is known to improve skin elasticity, promote formation of the basement membrane and thus adjust adhesion and proliferation of cells, improve a barrier function of selectively transmitting a harmful material, and provide an interaction of the epidermis and the dermis and the like. Accordingly, the migration and proliferation of the skin epidermis keratinocyte and the lead of the collagen synthesis improves skin elasticity as well as skin regeneration and wound healing and helps the skin keep healthy.

Recently, as an ozone layer has been destroyed due to rapid industrialization, and outdoor activity has been increased, skin damage due to ultraviolet (UV) has been increased and thus results in various diseases.

Conventionally, most of cosmetic compositions have an effect on skin moisturizing, whitening, wrinkle improvement, and the like but no effect on skin regeneration. Accordingly, research on development of a cosmetic composition having an effect of promoting skin regeneration through ultraviolet (UV)-blocking is increasingly required.

SUMMARY

An embodiment is to provide a cosmetic composition protecting a skin from ultraviolet (UV), and increasing expression levels of genes related to skin regeneration around the damaged skin due to radiation of the ultraviolet (UV) and thus promoting skin regeneration.

According to an embodiment, a cosmetic composition for skin regeneration includes a compound represented by Chemical Formula 1 as an active ingredient.

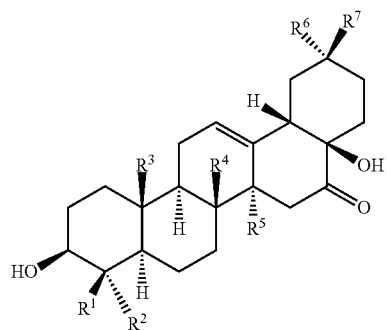

[Chemical Formula 1]

In Chemical Formula 1, $R^1$ to $R^7$ are independently a substituted or unsubstituted C1 to C20 alkyl group.

The compound represented by Chemical Formula 1 may be included at a concentration of 5 μM to 15 μM.

The compound represented by Chemical Formula 1 may be included at a concentration of 5 μM to 10 μM.

The compound represented by Chemical Formula 1 may be included at a concentration of 7.5 μM to 10 μM.

In Chemical Formula 1, $R^1$ to $R^7$ may independently be a methyl group.

The cosmetic composition for skin regeneration may be an ultraviolet (UV) blocking composition for the skin.

According to another embodiment, a method for regenerating skin by applying a cosmetic composition including an effective amount of the compound of Chemical Formula 1 as an active ingredient to the skin is provided.

According to an embodiment of the one aspect of the present disclosure, a cosmetic composition for skin regeneration blocks ultraviolet (UV) radiation into a skin and thus prevents skin damage and simultaneously, imparts a skin regeneration effect to the damaged skin by the ultraviolet (UV).

BRIEF DESCRIPTION OF THE DRAWINGS

FIGS. 1 and 2 are graphs independently showing levels of gene expression involved in wound healing for each of the treated group and untreated group of the compound represented by Chemical Formula 1. FIG. 2 is a graph showing an AQP-3 gene expression level.

FIGS. 3 and 4 are graphs independently showing each cell proliferation-related gene expression level (mRNA expression level) in a treatment group and a non-treatment group with a compound represented by Chemical Formula 1. FIG. 4 is a graph showing a K5 gene expression level.

FIGS. 5 and 6 are graphs independently showing a concentration that the compound represented by Chemical Formula 1 exhibits cytotoxicity.

DETAILED DESCRIPTION

Hereinafter, example embodiments of one aspect of the present disclosure will be hereinafter described in detail.

However, these example embodiments are only exemplary and do not limit one aspect of the present disclosure. However, this disclosure may be embodied in many different forms and is not construed as limited to the example embodiments set forth herein.

In the present specification, the skin regeneration refers regenerating skins by increasing expression levels of wound healing related genes and cell proliferation related genes present in the skin damaged by ultraviolet light (UV) and also refers to blocking ultraviolet (UV) into skins. However, skin regeneration mentioned in the present specification has nothing to do with skin moisturizing, whitening, and wrinkle improvement.

In the present specification, it will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when specific definition is not otherwise provided, "substituted" refers to replacement of at least one hydrogen of a functional group of one aspect of the present disclosure by at least one substituent selected from a halogen atom (F, Br, Cl, or I), a hydroxy group, a nitro group, a cyano group, an amino group ($NH_2$, $NH(R^{200})$ or $N(R^{201})(R^{202})$) wherein $R^{200}$, $R^{201}$, and $R^{202}$ are the same or different, and are independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, "alkyl group" refers to a C1 to C20 alkyl group, and specifically a C1 to C15 alkyl group, "cycloalkyl group" refers to a C3 to C20 cycloalkyl group, and specifically a C3 to C18 cycloalkyl group, "alkoxy group" refers to a C1 to C20 alkoxy group, and specifically a C1 to C18 alkoxy group, "aryl group" refers to a C6 to C20 aryl group, and specifically a C6 to C18 aryl group, "alkenyl group" refers to a C2 to C20 alkenyl group, and specifically a C2 to C18 alkenyl group, "alkylene group" refers to a C1 to C20 alkylene group, and specifically a C1 to C18 alkylene group, and "arylene group" refers to a C6 to C20 arylene group, and specifically a C6 to C16 arylene group.

As used herein, when specific definition is not otherwise provided, "(meth)acrylate" means both "acrylate" and "methacrylate," and "(meth)acrylic acid" means both "acrylic acid" and "methacrylic acid."

As used herein, when a definition is not otherwise provided, "combination" refers to mixing or copolymerization. Also, "copolymerization" refers to block copolymerization or random copolymerization, and "copolymer" refers to a block copolymer or a random copolymer.

As used herein, when a definition is not otherwise provided, hydrogen is bonded at the position when a chemical bond in chemical formulae is not drawn where supposed to be given.

As used herein, when a definition is not otherwise provided, "*" refers to a linking portion between the same or different atoms, or chemical formulae.

Hereinafter, a cosmetic composition for skin regeneration according to an embodiment is described.

A cosmetic composition for skin regeneration according to an embodiment includes a compound represented by Chemical Formula 1 as an active ingredient.

[Chemical Formula 1]

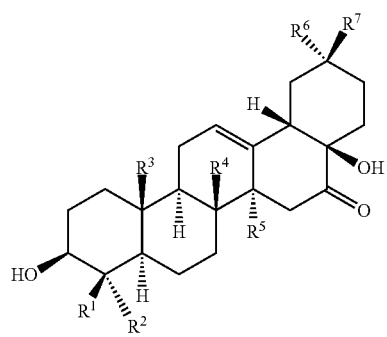

In Chemical Formula 1,
$R^1$ to $R^7$ are independently a substituted or unsubstituted C1 to C20 alkyl group.

The compound represented by Chemical Formula 1 is a *Camellia japonica* extract (camellenodiol) and may increase expression levels of several skin regeneration-related genes (AQP3 (Aquaporin-3), PPAR-α (peroxidase proliferator-activated receptor-alpha), PPAR-β (peroxidase proliferator-activated receptor-beta), K5 (Cytokeratin 5), K14 (Cytokeratin 14)) and thus have an excellent effect on skin regeneration and particularly, regeneration of the damaged skin by ultraviolet (UV). For example, in Chemical Formula 1, $R^1$ to $R^7$ may be independently methyl groups.

The compound represented by Chemical Formula 1 is a component infinitesimally present in *Camellia japonica*, which may be prepared by obtaining an extract through a filtration and a concentration under a reduced pressure after extracting a large amount of dried *Camellia japonica* with water-soluble ethanol and then, purifying the extract into a minute amount of camellenodiol by using HP-20 and silica chromatography. One aspect of the present disclosure is not limited to this extraction/purification method. The extraction/purification method for purifying a natural extract may include all the methods modified by a person who has an ordinary skill in the related art, and herein, various extraction/purification methods are publicly known and thus will not be illustrated in detail in the present specification.

One aspect of the present disclosure establishes that the compound represented by Chemical Formula 1 extracted from *Camellia japonica* includes components showing the aforementioned physiological activity, which show an effect of proliferation and migration of epidermis keratinocyte (refer to FIGS. 1 to 4). Specifically, the cosmetic composition for skin regeneration according to an embodiment may be a composition for blocking ultraviolet (UV) against a skin.

Accordingly, an embodiment provides the cosmetic composition for skin regeneration including the compound represented by Chemical Formula 1 as an active ingredient, which includes the compound represented by Chemical Formula 1 in a pharmaceutically effectively amount alone or along with at least one pharmaceutically acceptable carrier, excipient, or diluent.

When the compound represented by Chemical Formula 1 is used as a cosmetic composition for skin regeneration, the compound represented by Chemical Formula 1 may be used at a concentration of greater than or equal to 5 µM, greater than or equal to 7.5 µM. The compound represented by Chemical Formula 1 may be used at a concentration of less than or equal to 15 µM, less than or equal to 10 µM. When the compound represented by Chemical Formula 1 is used at a concentration of less than 5 µM, the compound has a little effect of proliferation and migration of epidermis keratinocyte and thus no effect of skin regeneration, but when the compound represented by Chemical Formula 1 is used at a concentration of greater than 15 µM, the compound may exhibit cytotoxicity and thus do damage to a human body.

As used herein, "pharmaceutically effective amount" refers to an amount sufficient to allow the physiologically active ingredient to be administered to an animal or human to exhibit desired physiological or pharmacological activity. However, the effective amount of the pharmaceutical may vary according to the degrees of symptoms, ages, weights, health status, sexes, administration routes, and duration of treatment.

In addition, "pharmaceutically acceptable" refers to a physiologically acceptable and administered to humans, usually does not cause allergic reactions or similar reactions, such as gastrointestinal disorders, dizziness. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils. In addition, it may further include fillers, anti-coagulants, lubricants, wetting agents, fragrances, emulsifiers, and antiseptics.

In the present specification "cosmetic" may refer to any material that may have a medical function in addition to the cosmetic function, in addition to the cosmetic function.

The chemical formulation of the cosmetic composition for skin regeneration is not particularly limited and may be appropriately selected as desired.

For example, the cosmetic composition for skin regeneration may be formulated into chemical formulations such as solutions, suspend liquid, emulsions, pastes, gels, creams, lotions, powders, soaps, surfactant-containing cleansings, oils, powder foundations, emulsion foundations, wax foundations, and sprays, but is not limited thereto. More specifically, it may be formulated into cosmetic compositions detergents, tonics, hair dressings, nourishing lotions, essences, serums, treatments, conditioners, shampoos, lotions, wools, or hair dyes, and the like, and may be formulated into chemical formulations such as oil-in-water (O/W) type, water-in-oil (W/O), and the like. In addition, in the composition, in addition to the above-mentioned essential components in each chemical formulation, other components may be appropriately selected and formulated without difficulty by a person of an ordinary skill in the art according to types or use purposes of other external preparations. For example, ultraviolet (UV) blocking agents, hair conditioning agents, fragrances, and the like may be further included.

The cosmetic composition for skin regeneration may include a cosmetically acceptable medium or base. These are all chemical formulations suitable for topical applications. The cosmetic composition may be provided in the forms of emulsions obtained by dispersing an oil phase in an aqueous phase, suspensions, microemulsions, microa capsules, microgranules, or ion-type (liposome) and/or non-ionized vesicle dispersing agents or in the forms of creams, skins, lotions, powders, ointments, sprays, or concealed sticks. These compositions may be prepared according to conventional methods in the art.

When the chemical formulation of one aspect of the present disclosure is a solution or emulsion, a solvent, a solubilizer, or an emulsifier may be used as carrier components. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan may be used.

If the chemical formulation of one aspect of the present disclosure is a suspension, the carrier component may be a diluent of a liquid such as water, ethanol or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, Agar, or tracant and the like.

If the chemical formulation of one aspect of the present disclosure is pastes, creams, or gels, the carrier component may be animal oil, vegetable oil, wax, paraffin, starch, tracant, cellulose derivatives, polyethylene glycol, silicone, bentonite, silica, talc or zinc oxide.

If the chemical formulation of one aspect of the present disclosure is powders or sprays, the carrier component may be lactose, talc, silica, aluminum hydroxide, calcium silicate or polyamide powders may be used. Particularly, in the case of sprays, a propellant such as chlorofluorohydrocarbon, propane/butane, or dimethyl ether may be additionally included.

In an embodiment of one aspect of the present disclosure, it may include thickeners in addition to the cosmetic composition for skin regeneration. The thickeners included in the cosmetic composition for skin regeneration of one aspect of the present disclosure may be methyl cellulose, carboxyl methyl cellulose, carboxyl methyl hydroxy guanine, hydroxy methyl cellulose, hydroxyethyl cellulose, carboxyl vinyl polymer, polyquaternium, cetearyl alcohol, stearic acid, and carrageenan. Preferably one or more of carboxyl methyl cellulose, carboxyl vinyl polymer, polyquaternium may be used, and most preferably a carboxyl vinyl polymer may be used.

In an embodiment of one aspect of the present disclosure, the cosmetic composition for skin regeneration may include a variety of suitable bases and additives as needed, and the types and amounts of these components may be easily selected by the inventor. If necessary, it may include an acceptable additive, and may further include for example, conventional ingredients such as antiseptics, pigments, additives, and the like.

The antiseptics may be specifically phenoxyethanol or 1,2-hexanediol, and the fragrances may be artificial flavors.

In an embodiment of one aspect of the present disclosure, the cosmetic composition for skin regeneration may include a composition selected from water-soluble vitamin, oil-soluble vitamin, polymeric peptide, polymeric polysaccharide, sphingolipid, and seaweed extract. Other ingredients that may be added include fats and oils, humectants, emollients, surfactants, organic and inorganic pigments, organic powders, ultraviolet (UV) absorbers, antiseptics, fungicides, antioxidants, plant extracts, pH adjusters, alcohols, pigments. fragrances, blood circulation accelerators, coolants, anhidrotics, purified water, and the like.

In addition, the compounding components which may be added other than these are not limited thereto. Moreover, any component may be blended in the range which does not damage the purpose and effect of embodiment of the invention.

Furthermore, the cosmetic composition according to an embodiment may be used not only as a pharmaceutical composition as described above, but also as a dietary supplement. For example, it may be easily used as main ingredients, auxiliary ingredients, food ingredients, food additives, functional foods, or beverages.

The "food" means a natural or processed product including one or more nutrients, preferably means that it is ready to be eaten directly after a certain amount of processing. It includes all foods, food additives, functional foods, and a beverage.

The foods to which the food composition can be added may include for example, various foods, a beverage, gum, tea, vitamin composites, and functional foods. In addition, special nutritional products (e.g., delicatessen, young, baby food, etc.), processed meat products, fish products, tofu, jelly, noodles (e.g. ramen, noodles, etc.), breads, dietary supplements, seasoned foods (e.g., soy sauce, Miso, red pepper paste, mixed soy sauce, etc.), sources, sweets (e.g. snacks), candy, chocolate, gum, ice cream, dairy products (e.g. fermented milk, cheese, etc.), other processed foods, kimchi, pickles (various kimchi, pickles, etc.), a beverage (e.g., fruit beverage, vegetable beverage, soy milk, fermented beverage, etc.), natural seasonings (e.g., ramen soup, etc.). The foods, beverages, or food additives may be prepared by conventional manufacturing methods.

In addition, the "functional foods" or "health functional foods" refers to a food group that has added values to foods by using physical, biochemical, or biotechnological techniques to act and express functions of foods for specific purposes, or foods that are processed and designed to fully express body's regulatory functions, such as defense rhythm control of food compositions, disease prevention and recovery to living bodies. It may be specifically a health functional food. The functional food may include acceptable food auxiliary additives and may further include suitable carriers, excipients, and diluents commonly used in the manufacture of functional foods.

The types of dietary supplements are not limited thereto, but may be in a form of powders, granules, tablets, capsules, or beverages.

According to another embodiment, a method for regenerating skin by applying a cosmetic composition including an effective amount of the compound represented by Chemical Formula 1 as an active ingredient to the skin is provided.

Advantages and features of one aspect of the present disclosure and methods for achieving them will be apparent with reference to the examples described below in detail. One aspect of the present disclosure will be described in detail with reference to examples. However, these examples are specifically provided for describing one aspect of the present disclosure, and the range of one aspect of the present disclosure is not limited to these examples.

EXAMPLES

Skin Regeneration Effect After Ultraviolet (UV) Irradiation

A human keratinocyte cell line (HaCaT cells) was irradiated with ultraviolet (UVA) (2 J/cm$^2$, 3 J/cm$^2$) and then, treated with a compound represented by Chemical Formula 1-1 (camellenodiol), which was obtained by extracting 10 kg of dry camellia powder with water-soluble ethanol and subsequently, performing filtration, concentration under a reduced pressure, and purification by using HP-20 and silica chromatography, to exam AQP3, PPAR-α, PPAR-β, K5, and K14 gene level changes, and the results are shown in FIGS. 1 to 4. Referring to FIGS. 1 to 4, comparing before the irradiation with ultraviolet (UV) (CTL) with after the irradiation with ultraviolet (UVA) (2 J/cm$^2$, 3 J/cm$^2$), the genes (AQP3, PPAR-α, PPAR-β) known to be important for cutaneous wound healing and the genes (K5, K14) playing an important role of cell proliferation of an epidermis stratum basal were decreased, but when treated with the compound represented by Chemical Formula 1-1 (CMD), levels of the genes were significantly increased within a concentration of 5 μM to 10 μM and specifically, 7.5 μM. Specifically, as for the irradiation with a relatively smaller dose of ultraviolet (UVA) (2 J/cm$^2$), when the compound represented by Chemical Formula 1-1 was used within a concentration of 7.5 μM to 10 μM, an excellent skin regeneration effect was obtained, but as for the irradiation with a relatively large dose of ultraviolet (UVA) (3 J/cm$^2$), when the compound represented by Chemical Formula 1-1 was used within a concentration of 5 μM to 7.5 μM, an excellent skin regeneration effect was obtained.

[Chemical Formula 1-1]

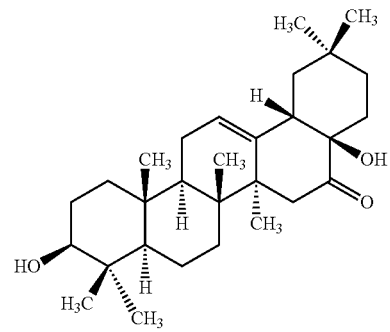

(Average mass: 442.674 Da)
(Monoisotopic mass: 442.344696 Da)

Cytotoxicity Evaluation

A cytotoxicity evaluation of the compound represented by Chemical Formula 1-1 was twice performed by using a serum-free media, and the results are shown in FIGS. 5 and 6. Referring to FIGS. 5 and 6, a significant cytotoxicity concentration of the compound represented by Chemical Formula 1-1 was 20 μM (cell viability<80%). In other words, when the compound represented by Chemical Formula 1 had a concentration of 20 μM, cytotoxicity thereof might do damage to a human body, and accordingly, the concentration of the compound represented by Chemical Formula 1 may be limited to be less than or equal to 10 μM.

Although the preferred embodiments of one aspect of the present disclosure have been described in detail above, the scope of one aspect of the present disclosure is not limited thereto. Various modifications and improvements of those skilled in the art using the basic concepts of one aspect of the present disclosure defined in the following claims belong to the scope of embodiment of the invention.

The invention claimed is:

1. A cosmetic composition, comprising
a compound of Chemical Formula 1 as an active ingredient:

Chemical Formula 1

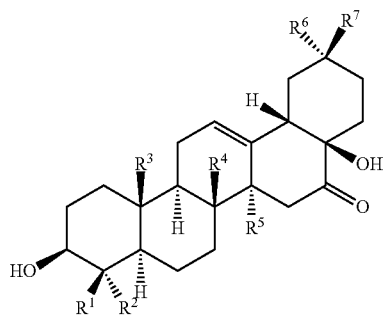

wherein, in Chemical Formula 1,
R¹ to R⁷ are independently a substituted or unsubstituted C1 to C20 alkyl group.

2. The cosmetic composition of claim 1, wherein the compound of Chemical Formula 1 is included at a concentration of 5 μM to 15 μM.

3. The cosmetic composition of claim 2, wherein the compound of Chemical Formula 1 is included at a concentration of 5 μM to 10 μM.

4. The cosmetic composition of claim 3, wherein the compound of Chemical Formula 1 is included at a concentration of 7.5 μM to 10 μM.

5. The cosmetic composition of claim 1, wherein R¹ to R⁷ are independently a methyl group.

6. The cosmetic composition of claim 1, wherein the cosmetic composition blocks an ultraviolet (UV).

7. A method for regenerating skin of a subject by applying an effective amount of the cosmetic composition of claim 1 to the skin.

8. The method of claim 7, wherein the compound of Chemical Formula 1 is included at a concentration of 5 μM to 15 μM in the cosmetic composition.

9. The method of claim 7, wherein the compound of Chemical Formula 1 is included at a concentration of 5 μM to 10 μM in the cosmetic composition.

10. The method of claim 7, wherein the compound of Chemical Formula 1 is included at a concentration of 7.5 μM to 10 μM in the cosmetic composition.

11. The method of claim 1, wherein R¹ to R⁷ are independently a methyl group.

12. The method of claim 7, wherein the cosmetic composition blocks an ultraviolet (UV).

* * * * *